United States Patent [19]

Leyshon et al.

[11] Patent Number: 5,026,936
[45] Date of Patent: Jun. 25, 1991

[54] ENHANCED PRODUCTION OF PROPYLENE FROM HIGHER HYDROCARBONS

[75] Inventors: David W. Leyshon; John A. Sofranko, both of West Chester; C. Andrew Jones, Newtown Square, all of Pa.

[73] Assignee: Arco Chemical Technology, Inc., Wilmington, Del.

[21] Appl. No.: 415,747

[22] Filed: Oct. 2, 1989

[51] Int. Cl.[5] ............................................. C07C 4/06
[52] U.S. Cl. .................................... 585/315; 585/324; 585/643; 585/644; 585/648; 585/650; 585/651; 585/653
[58] Field of Search ............... 585/315, 324, 643, 644, 585/648, 650, 651, 653

[56] References Cited

U.S. PATENT DOCUMENTS

| 3,431,316 | 3/1969 | Banks | 585/643 |
| 4,172,816 | 10/1979 | Pop et al. | 585/653 |
| 4,613,721 | 9/1986 | Kaiser | 585/650 |

FOREIGN PATENT DOCUMENTS 0109059 5/1984 European Pat. Off. .

Primary Examiner—Curtis R. Davis
Attorney, Agent, or Firm—William C. Long

[57] ABSTRACT

The present invention provides a process for the preparation of propylene from $C_4$ or higher feed by a combination of cracking and metathesis wherein higher hydrocarbon is cracked to form ethylene and propylene and at least a portion of the ethylene is metathesized to propylene.

1 Claim, 1 Drawing Sheet

ENHANCED PRODUCTION OF PROPYLENE FROM HIGHER HYDROCARBONS

BACKGROUND OF THE INVENTION

1. Field of the Invention

The present invention provides an improved method for the production of propylene from a $C_4$ or higher hydrocarbon feed. Specifically, in accordance with the invention, a higher hydrocarbon is converted over a zeolite catalyst at conditions which favor production of a product mixture containing ethylene and propylene. Propylene is separated from this product mixture and recovered. The ethylene from the reaction mixture is metathesized with $C_4+$olefin in order to form further quantities of product propylene.

2. Description of the Prior Art

Propylene is an important chemical of commerce. In general, propylene is largely derived from selected petroleum feed materials by procedures such as steam cracking which also produce high quantities of other materials. At times, there exist shortages of propylene which result in uncertainties in feed supplies, rapidly escalating raw material costs and similar situations which are undesirable from a commercial standpoint. Also, due to imbalances in hydrocarbon values, economics favor using alternate feedstocks provided an effective process for forming propylene was available.

Methods are known for the conversion of higher hydrocarbons to reaction mixtures comprised of the $C_2$ and $C_3$ lighter olefins. For example, published European patent applications Publication Nos. 0109059 and 0109060 provide illustrative teachings of conditions and catalysts which are effective for the conversion of higher hydrocarbons such as butenes to the lighter olefins. Copending application Ser. No. 07/343097, filed Apr. 25, 1989, likewise provides a comprehensive teaching of prior methods for the production of the lower olefins from higher hydrocarbon feed materials. In certain instances, it would be distinctly advantageous to provide means for still further improving yields of propylene which result from the conversion of less expensive higher hydrocarbon feed materials.

The disproportionation or metathesis of olefins is likewise a known reaction. In this regard, reference can be made to Banks U.S. Pat. No. 3,261,879, to Banks "Olefin Metathesis Technology and Application," *Applied Industrial Catalysis*, Volume III, Chapter 7, Pages 215, et seq., Leach, Editor (1984). In addition, olefin metathesis reaction and catalysts useful therefor are described in U.S. Pat. Nos. 3,883,606, 3,915,897, 3,952,070, 4,180,524, 4,431,855, 4,499,328, 4,504,694, 4,517,401 and 4,547,617.

Despite developments in the art, it remains desirable to provide methods for producing higher yields of propylene from the less expensive higher hydrocarbon feed materials.

SUMMARY OF THE INVENTION

The present invention provides an improved process for the selective production of propylene from $C_4$ and higher hydrocarbons, especially from $C_4$ and higher olefins and paraffins. In accordance with the invention, in a first step, the higher olefin and/or paraffin hydrocarbon is reacted over a zeolitic type catalyst at conditions selected to produce high yields of ethylene and propylene. Propylene from this reaction is recovered as a product of the process. In order to enhance propylene yields, ethylene from the zeolite conversion reaction is passed to a metathesis reaction zone wherein it is metathesized with $C_4+$olefin to produce further quantities of the desired propylene product.

DESCRIPTION OF DRAWING

The attached drawing illustrates in schematic fashion practice of the invention.

DETAILED DESCRIPTION OF THE INVENTION

Figure 1:
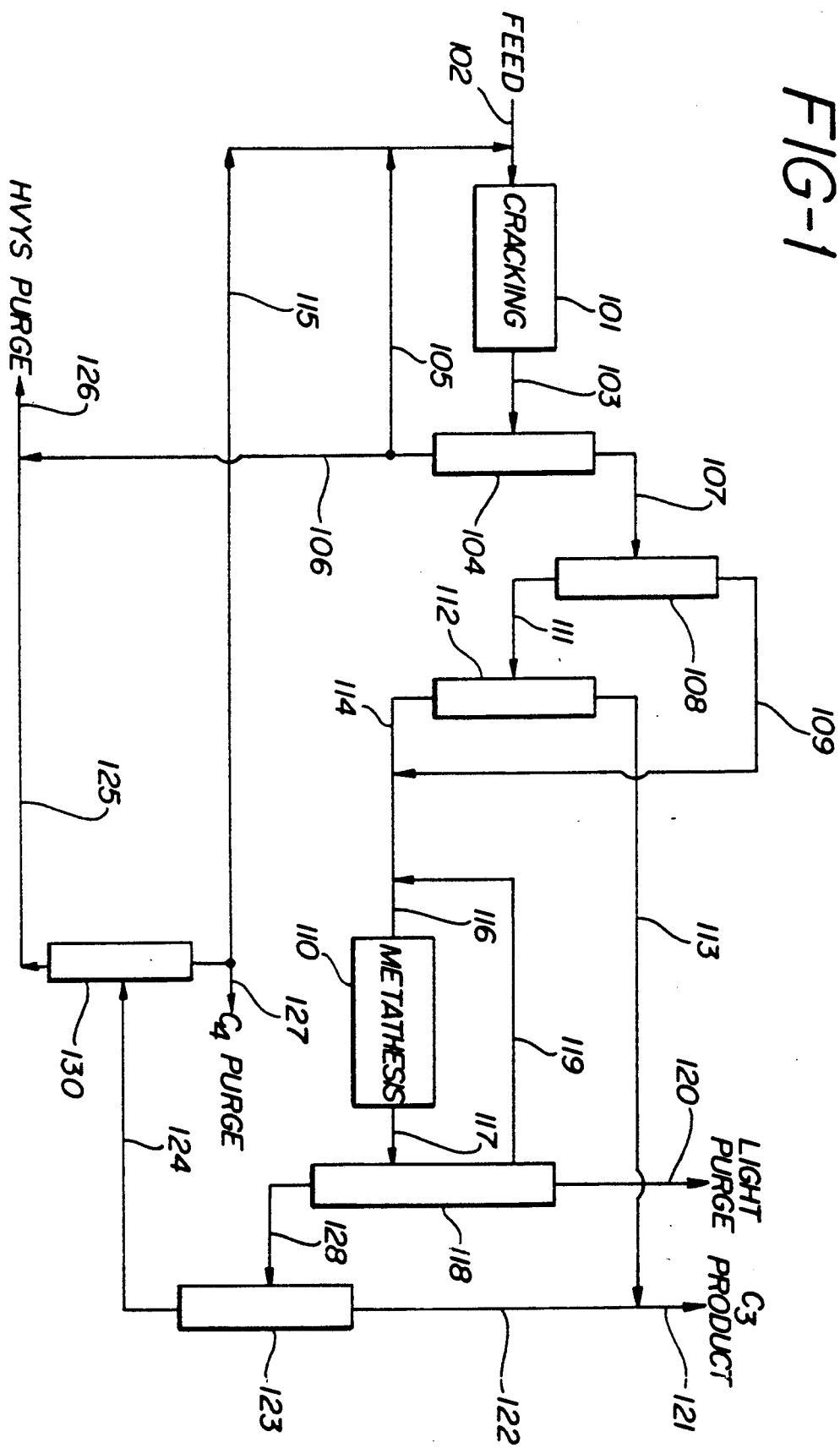

In accordance with the present invention, the higher hydrocarbon feed stock, preferably butenes and/or higher olefins and/or paraffins, is reacted under conditions which favor the production of lower olefins. These conditions generally involve low hydrocarbon partial pressure and high reaction temperatures. The product mixture from this reaction is separated into various components. The propylene component comprises a product of the process. The ethylene component is passed to a metathesis zone in admixture with a higher olefin such as butene, also contained in the reaction mixture.

The ethylene metathesis is carried out under conditions and using catalysts which are known in the art. Generally, a catalyst containing a catalytic amount of at least one of molybdenum oxide and tungsten oxide is suitable for the metathesis reaction. Conditions of the metathesis generally include reaction temperatures ranging from about 100° to about 450° C., preferably 150° to 350° C., and pressures varying from about atmospheric to upwards of 3,000 psig, although higher pressures can be employed if desired.

Catalysts which are active for the metathesis of olefins and which can be used in the process of this invention are of a generally known type. In this regard, reference is made to "Journal of Molecular Catalysis", 28 (1984) pages 117–131, to "Journal of Catalysis", 13 (1969) pages 99–113, to "Applied Catalysis" 10 (1984) pages 219–229 and to "Catalysis Reviews", 3 (1) (1969) pages 37–60.

Such catalysts may be homogeneous or heterogeneous, with heterogeneous catalysts being preferred. The catalyst preferable comprises a catalytically effective amount of a transition metal component. The preferred transition metals for use in the present invention include tungsten, molybdenum, nickel, rhenium and mixtures thereof. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components, or the lower olefin component conversion. Preferably, the support material is an oxide, such as silica, alumina, titania, zirconia and mixtures thereof. Silica is a particularly preferred support material. If a support material is employed, the amount of transition metal component used in combination with the support material may vary widely depending, for example, on the particular application involved and/or the transition metal being used. Preferably, the transition metal comprises about 1% to about 20%, by weight (calculated as elemental metal) of the total catalyst.

The metathesis catalysts advantageously comprise a catalytically effective amount of at least one of the above-noted transition metals, and are capable of promoting olefin metathesis.

Preferably, the metathesis catalyst further comprises at least one activating agent present in an amount to improve the effectiveness of the catalyst. Various activating agents may be employed, including activating agents which are well known in the art to facilitate metathesis reactions. Preferred activating agents include organo-metallic compounds, such as tetra methyl tin, oxides, such as alkaline earth metal oxides, alumina and silica and mixtures thereof. In one particular embodiment, when the activating agent is at least one oxide, the activating agent may be used as a support for the transition metal component. If an organo-metallic activating agent is employed the agent may be included with the catalyst during catalyst preparation, or it may be added during reaction. Preferably, the amount of organo-metallic activating agent is relatively minor compared to the amount of catalytically active metal component in the first catalyst.

The metathesis mixture is resolved by conventional separation means into a light ethylene fraction which can be recycled, a product propylene fraction, and a butene and higher hydrocarbon fraction which is preferably recycled to the higher hydrocarbon conversion zone for the production of further amounts of ethylene and propylene, and to metathesis.

The specified combination of the conversion of the higher hydrocarbons to a mixture comprised of ethylene and propylene at conditions favoring the production of these components coupled with the use of the thus formed ethylene to produce further quantities of desired propylene provides a synergistic combination of reaction steps whereby there are obtained substantially improved yields of the desired light olefin, propylene, from inexpensive and readily available higher hydrocarbon feed materials.

Referring to FIG. 1, feed hydrocarbon is introduced into cracking zone 101 via line 102. The feed hydrocarbon can be olefinic or paraffinic, or mixtures of olefins and paraffins can be used. Preferably $C_4$ and higher hydrocarbons are used, examples being butane, the butenes, hexane, hexenes, methyl pentanes, methyl pentenes, cetane, petroleum naphtha fractions and the like.

In zone 101, the hydrocarbon feed, plus any recycle as hereinafter described, is cracked over a zeolitic catalyst such as ZSM-5 at conditions selected to form light olefin product. The conversion is carried out at temperatures in the range of about 400° to 800° C., preferably 500° to 700° C. Low hydrocarbon partial pressures and low conversions per pass favor the lower olefin formation. The hydrocarbon can be admixed with steam or inert gas such as nitrogen. The hydrocarbon partial pressure is as low as practical, illustratively 1 to 30 psia. Where no diluents are employed, system pressures ranging from about $-12$ to 50 psig, preferably $-5$ to 30 psig are suitable. Higher pressures can be used when diluents are employed.

High space velocity and short residence times are preferred in order to maintain the desired low conversions per pass. Space velocities are 1 to 5000, preferably 5 to 2000 hr.$^{-1}$ WHSV.

Fixed bed reactions can be used, but fluidized solid procedures are preferred.

Zeolite catalysts used in the invention can be silaceous, crystalline molecular sieves. Such silica-containing crystalline materials include materials which contain, in addition to silica, significant amounts of alumina. These crystalline materials are frequently named "zeolites, i.e., crystalline aluminosilicates." Silica-containing crystalline materials also include essentially aluminum-free silicates. These crystalline materials are exemplified by crystalline silica polymorphs (e.g., silicalite, disclosed in U.S. Pat. No. 4,061,724 and organosilicates, disclosed in U.S. Pat. No. Re. 29948), chromia silicates (e.g., CZM), ferrosilicates and galliosilicates (see U.S. Pat. No. 4,238,318), and borosilicates (see U.S. Pat. Nos. 4,226,420; 4,269,813; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246).

Acid aeolites are especially preferred, particularly the ZSM type and borosilicates. ZSM-5 is especially useful.

Phosphorous-containing zeolites such as are described in U.S. Pat. No. 3,972,832 are also especially useful.

In addition to the above, zeolite-containing materials can be used. Representative of such materials are zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), synthetic mordenite, and dealuminized mordenite as well as naturally occurring zeolites, including chabazite, faujasite, mordenite and the like.

In general, the zeolites are ordinarily ion-exchanged with a desired cation to replace alkali metal present in the zeolite as found naturally or as synthetically prepared. The exchange treatment is such as to reduce the alkali metal content of the final catalyst to less than about 0.5 weight percent. Preferred exchanging cations are hydrogen, ammonium, rare earth metals and mixtures thereof, with particular preference being accorded rare earth metals. Ion exchange is suitably accomplished by conventional contact of the zeolite with a suitable salt solution of the desired cation, such as, for example, the sulfate, chloride or nitrate salts.

It is preferred to have the crystalline zeolite of a suitable matrix, since the catalyst form is generally characterized by a high resistance to attrition, high activity and exceptional steam stability. Such catalysts are readily prepared by dispersing the crystalline zeolite in a suitable siliceous sol and gelling the sol by various means. The inorganic oxide which serves as the matrix in which the above crystalline zeolite is distributed includes silica gel or a cogel of silica and a suitable metal oxide. Representative cogels include silica-aluminia, silica-magnesia, silica-zirconia, silica-thoria, silica-beryllia, silica-titania as well as ternary combinations, such as silica-alumina-magnesia, silica-aluminia-zirconia and silica-magnesia-sirconia. Preferred cogels include silica-alumina, silica-zirconia or silica-alumina-zirconia. The above gels and cogels will generally comprise a major proportion of silica and a minor proportion of the other aforementioned oxide or oxides. Thus, the silica content of the siliceous gel or cogel matrix will generally fall within the range of 55 to 100 weight percent, preferably 60 to 95 weight percent, and the other metal oxide or oxides content will generally be within the range of 0 to 45 weight percent. In addition to the above, the matrix may also comprise natural or synthetic clays, such as kaoline type clays, montmorillonite, bentonite or halloysite. These clays may be used either alone or in combination with silica or any of the above specified cogels in a matrix formulation.

From zone 101, the reaction mixture passes via line 103 to separation zone 104. In zone 104, the reaction mixture from zone 101 is separated by conventional distillation procedures into an overhead fraction comprised of $C_4$ and lighter components and a heavier bottoms fraction. The bottoms fraction is removed via line 105 and recycled to zone 101, a small purge stream being separated via line 106.

A side draw of heavy olefins (not shown) may be removed from zone 104 and sent to metathesis (zone 110). This may be desirable for raising the propylene yield in metathesis.

The overhead fraction, comprised primarily of ethylene, propylene and $C_4$ saturated and unsaturated components, passes via line 107 to separation zone 108. In zone 108, an ethylene fraction is separated overhead by conventional distillation and passes via lines 109 and 116 to metathesis zone 110. A bottoms fraction comprised of $C_3$ and $C_4$ components is removed from zone 108 via line 111 and passes to separation zone 112. In zone 112, the mixture is separated by conventional distillation into an overhead product propylene stream which is recovered via lines 113 and 121 and a primarily $C_4$ fraction which is removed via line 114. The $C_4$ fraction is combined with ethylene from lines 109 and 119 and passes via lines 114 and 116 to metathesis zone 110. In zone 110, the mixture of ethylene and $C_4$ olefins is metathesized in order to form additional product propylene.

The metathesis reaction product mixture passes from zone 110 via line 117 to separation zone 118 wherein by conventional distillation a light purge stream suitable as fuel gas is separated overhead via line 120. Zone 118 has a side draw, line 119, for separation and recycle of unconverted ethylene to metathesis.

A $C_3$+ stream is removed from zone 118 via line 128 and passes to separation zone 123. By conventional distillation, product propylene is separated overhead via line 122, combined with propylene via line 113 and recovered via line 121.

A $C_4$ and higher fraction is recovered from zone 123 via line 124 and passed to separation zone 130 wherein by distillation a $C_4$ fraction is separated overhead from a heavier fraction which is removed via line 125, combined with the heavies purge via line 106 and purged via line 126.

A portion of the overhead $C_4$ fraction from zone 130 is purged via line 127 in order to prevent paraffins buildup. The remainder is passed via line 115 to cracking zone 101.

Although not shown, it is usually desirable to hydrotreat the feed to the metathesis zone 110 in order to convert coke formers such as diolefins and acetylene compounds and thus avoid rapid deactivation of the metathesis catalyst.

Propylene yields as high as 60% based on the carbon content of the higher hydrocarbon feed can be achieved. The process requires no extraordinary catalysts, materials or construction, reaction conditions, and the like.

The following example, with special reference to the attached drawing, serves to more fully illustrate practice of the invention. In the example, parts are 1000 lbs. per hour unless otherwise indicated.

EXAMPLE 1

Referring to FIG. 1, $C_4$ Raffinate II feed in amount of 92.3 parts is fed via line 102 to cracking zone 101. Combined with the fresh Raffinate is a stream from separation zone 130 passing via line 115 to line 102 and thence to zone 101, and a stream from separation zone 104 passing via line 105 to line 102 and thence to zone 101.

The combined hydrocarbons mixture is contacted with a ZSM-5 catalyst in zone 101. Temperature is 550° C. and space velocity is 40 hr.$^{-1}$ WHSV. Conditions in zone 101 favor the formation of lower olefins.

The reaction mixture from zone 101 containing ethylene and propylene passes via line 103 to separation zone 104.

An overhead fraction comprised of $C_4$ and lighter components passes from zone 104 via line 107 to separation zone 108. A heavier $C_5$+ fraction is recycled via line 105, a purge stream being separated via lines 106 and 126.

The overhead from zone 104 passes to distillation zone 108 wherein an ethylene fraction is separated overhead and passed via lines 109 and 116 to metathesis zone 110. A bottom $C_3$+ stream passes via line 111 to distillation zone 112; from zone 112, product propylene is separated overhead by distillation and recovered via lines 113 and 121.

A $C_4$ stream is removed from zone 112 and passes via lines 114 and 116 to metathesis zone 110 along with ethylene via line 109 and recycle ethylene via line 119.

In zone 110, the ethylene and $C_4$= is contacted at metathesis conditions with a metathesis catalyst comprised of $WO_3$ supported in silica; temperature is 300° C. and space velocity is 25 hr.$^{-1}$ WHSV.

The metathesis product mixture passes via line 117 to distillation separation zone 118; a light purge stream is separated overhead by conventional distillation and separated via line 120. A sidestream of ethylene is separated and recycled to metathesis via lines 119 and 116. A $C_3$+ stream is removed as bottoms and passes to distillation zone 123.

By conventional distillation, product propylene is separated overhead and recovered via lines 122 and 121. A $C_4$+ fraction is removed via line 124 as bottoms and passes via line 124 to distillation zone 130.

By distillation, a $C_4$ overhead is removed with a portion purged via line 127 and the remainder recycled via lines 115 and 102 to cracking zone 101.

A heavies purge is removed via line 125 and purged via line 120.

The compositions of the various process and product streams expressed in 1000 pounds per hour is given in the following Table 1. (Table 1 is continued on next two pages):

TABLE 1

| | M POUNDS PER HOUR | | | | | | | | | | |
|---|---|---|---|---|---|---|---|---|---|---|---|
| | STREAM | | | | | | | | | | |
| COMPONENT | 102 | 103 | 105 | 106 | 107 | 109 | 111 | 113 | 114 | 115 | 116 |
| $CH_4 + H_2$ | | 1.6 | | | 1.6 | 1.6 | | | | | 2.4 |
| $C_2$= | | 8.9 | | | 8.9 | 8.9 | | | | | 20.7 |
| $C_2$ | | 1.1 | | | 1.1 | 1.1 | | | | | 11.5 |

TABLE 1-continued

M POUNDS PER HOUR

| Component | | | | | | | | | | |
|---|---|---|---|---|---|---|---|---|---|---|
| $C_3^=$ | | 30.4 | | | 30.4 | 30.4 | 30.4 | | | |
| $C_3$ | | 3.3 | | | 3.3 | 3.3 | 3.3 | | | |
| $iC_4^=$ | | 9.3 | | | 9.3 | 9.3 | | 9.3 | 3.8 | 9.3 |
| $nC_4^=$ | 78.4 | 20.7 | | | 20.7 | 20.7 | | 20.7 | 2.3 | 20.7 |
| Paraffin $C_4$ | 13.9 | 31.2 | | | 31.2 | 31.2 | | 31.2 | 15.6 | 31.2 |
| $C_5^+$ | | 38.1 | 30.6 | 7.5 | | | | | | |
| TOTAL | 92.3 | 144.6 | 30.6 | 7.5 | 106.5 | 11.6 | 94.9 | 33.7 | 61.2 | 21.7 | 95.8 |

| COMPONENT | STREAM | | | | | | | | |
|---|---|---|---|---|---|---|---|---|---|
| | 117 | 119 | 120 | 121 | 122 | 124 | 125 | 126 | 127 |
| $CH_4 + H_2$ | 2.4 | 0.8 | 1.6 | | | | | | |
| $C_2^=$ | 14.0 | 11.8 | 2.2 | | | | | | |
| $C_2$ | 11.5 | 10.4 | 1.1 | | | | | | |
| $C_3^=$ | 21.8 | | | 52.2 | 21.8 | | | | |
| $C_3$ | 0 | | | 3.3 | | | | | |
| $iC_4^=$ | 7.5 | | | | | 7.5 | | | 3.7 |
| $nC_4^=$ | 4.6 | | | | | 4.6 | | | 2.3 |
| Paraffin $C_4$ | 31.2 | | | | | 31.2 | | | 15.6 |
| $C_5^+$ | 2.8 | | | | | 2.8 | 2.8 | 10.3 | |
| TOTAL | 95.8 | 23.0 | 4.9 | 55.5 | 21.8 | 46.1 | 2.8 | 10.3 | 21.6 |

What is claimed is:

1. The method for the production of propylene which comprises:

(a) cracking a $C_4$ or higher olefin and/or paraffin hydrocarbon over a zeolite catalyst at conditions favoring production of ethylene and propylene to form a mixture comprised of ethylene, propylene and butene, (b) separating ethylene and butene from the step (a) reaction mixture, (c) metathesizing said separated ethylene and butene from the step (a) reaction mixture to form additional propylene, and (d) recovering propylene formed in step (a) and step (c).

* * * * *